(12) United States Patent
Mossel

(10) Patent No.: US 7,254,489 B2
(45) Date of Patent: Aug. 7, 2007

(54) SYSTEMS, METHODS AND APPARATUS FOR RECONSTRUCTING PHYLOGENTIC TREES

(75) Inventor: Elchanan Mossel, Jerusalem (IL)

(73) Assignee: Microsoft Corporation, Redmond, WA (US)

( * ) Notice: Subject to any disclaimer, the term of this patent is extended or adjusted under 35 U.S.C. 154(b) by 462 days.

(21) Appl. No.: 10/160,472

(22) Filed: May 31, 2002

(65) Prior Publication Data

US 2003/0225771 A1    Dec. 4, 2003

(51) Int. Cl.
*G01N 33/48* (2006.01)
*G06G 7/48* (2006.01)
(52) U.S. Cl. .......................................... 702/19; 703/11
(58) Field of Classification Search .................... 702/19
See application file for complete search history.

(56) References Cited

U.S. PATENT DOCUMENTS 6,128,587 A * 10/2000 Sjolander ....................... 703/2

OTHER PUBLICATIONS

Hendy et al. "A Discrete Fourier Analysis for Evolutionary Trees," Evolution, vol. 91, Apr. 1994, pp. 3339-3343.*
Crayan et al. "Evolutionary Trees Can be Learned in Polynomial Time in the Two-State General Markov Model," Society for Industral and Applied Mathematics, vol. 31. No. 2, pp. 375-397 (2001).*

* cited by examiner

*Primary Examiner*—John S. Brusca
*Assistant Examiner*—Jerry Lin
(74) *Attorney, Agent, or Firm*—Lee & Hayes, PLLC

(57) ABSTRACT

In one aspect, a tree data structure is reconstructed by reconstructing a local topology from samples of data of known nodes, and estimating the data value of each node in the reconstructed local topology. The reconstructing and estimating are performed iteratively. In another aspect, the topology is reconstructed from pairs of known nodes that are within a predetermined correlation, and using a four-point function. The number of samples of data that the topology is calculated from is a factor of a natural logarithm of the number of known nodes that are within a predetermined correlation. In another aspect, the estimating is performed using a majority function.

35 Claims, 8 Drawing Sheets

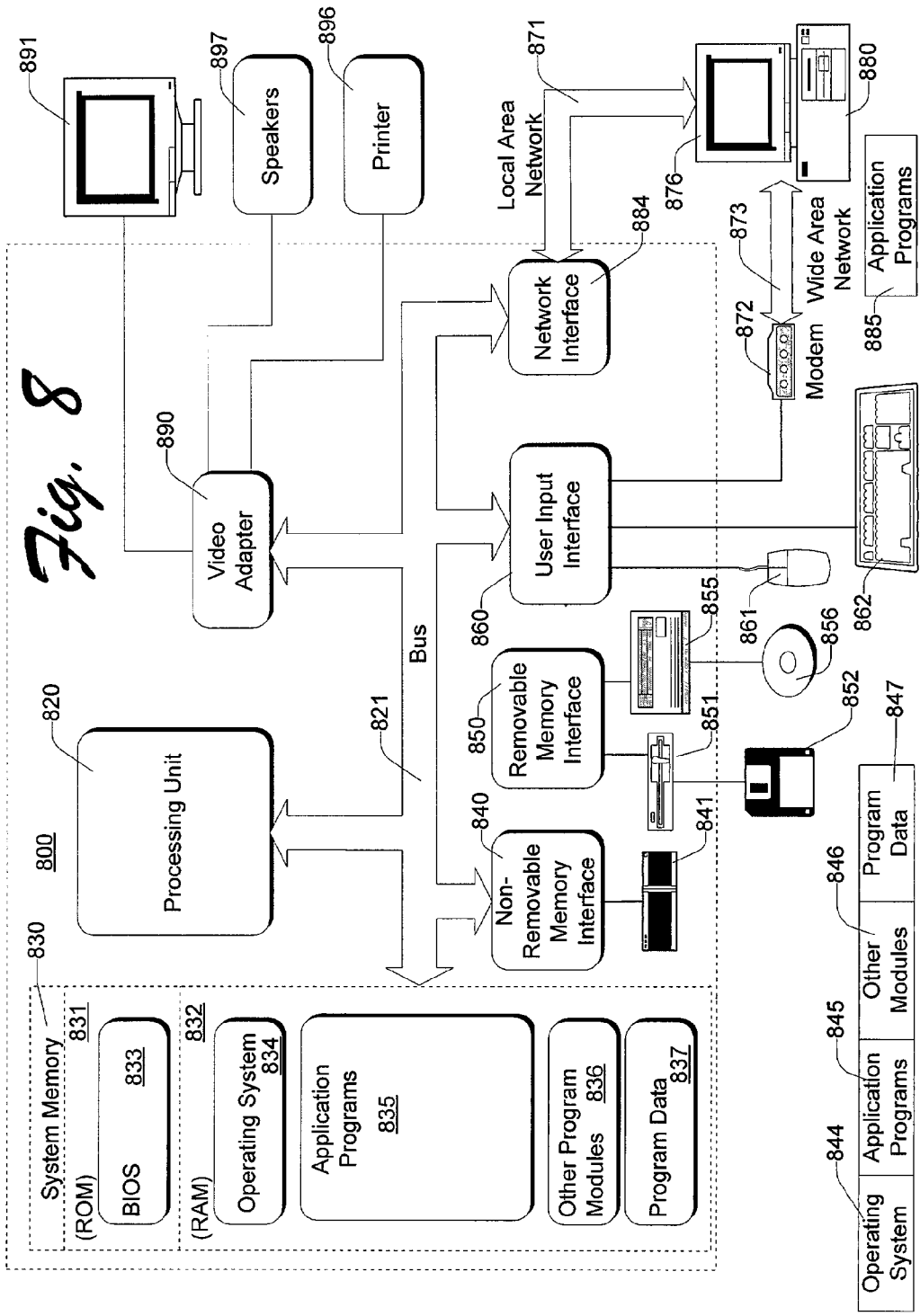

SYSTEMS, METHODS AND APPARATUS FOR RECONSTRUCTING PHYLOGENTIC TREES

TECHNICAL FIELD

This invention relates to tree data structures, and more particularly to reconstructing phylogenetic tree data structures from samples of data at vertices of the tree data structures.

BACKGROUND

Phylogenetics is the reconstruction of a pattern of events that have led to the distribution and diversity of life. The distribution and diversity of life is represented by a phylogenetic tree structure.

A phylogenetic tree is a representation of an evolution of species. FIG. 1 is a diagram of a complete phylogenetic tree structure. A phylogenetic tree is also known as a cladogram or a dendrogram. The tree structure includes vertices and edges. An individual organism or species is presented by a vertex, such as 100. Vertices are also known as nodes. Time is presented along the vertical dimension of the tree, in which lower vertices represent later generations of life. Edges, such as 102, connect vertices. When edges converge at a vertex, the point of convergence is the common ancestral species or ancestor. In phylogenetic trees in which each vertex represents a species, that vertex represents the point when the two species diverge from a common ancestral species. All inner nodes have degree of at least three. The degree of a node is the number of edges emanating from the node.

An approximation of how close two species or individuals are related is determined from a distance between species or individuals. Any two species or individuals have a unique most recent common ancestor in the tree. Two species or individuals are closely related if the common ancestor is recent and distantly related if the common ancestor is remote. To calculate a measure of the distance between species or individuals, the distances to their common ancestor are summed. A distance is the smallest count of edges between two vertices. For example, where an ancestor 104 occurs two time units in the past, then the distance between the two species or individuals, 106 and 108, would be four because two edges are traversed between the common ancestor 104 and each of the species or individuals. The four edges traversed between vertices 106 and 108 are 110, 112, 102, and 114, and yield a distance of 4.

Each individual has genetic properties represented by a string of characters or letters. The string of characters is represented by data in a corresponding vertex. For example, where a genetic property is a DNA sequence or sub-sequence, the property is represented by a string of characters selected from a group comprising the characters, "A," "C," "G" and "T." For example, a parent vertex 100 might have the DNA sub-sequence "GATCTT" and a child vertex 108 might have the DNA sub-sequence "GATATT."

Small mutations exist in the genetic properties between parent and child. The mutations are represented by differences in the character strings. When the topology of a phylogenetic tree is unknown, and thus the actual distance between vertices is unknown, the only possible way to reconstruct a tree is from the mutation between species or individuals. The more characters two organisms share, the closer they are presumed to be evolutionarily, and the closer together they should cluster on a phylogenetic tree.

Stochastic mutation models are used to model the mutations along phylogenetic tree. Stochastic mutation models include the Cavender, Farris and Neyman (CFN) model, the Kimura 2-parameter model, the Kimura 3-parameter model, and even more general stochastic models.

FIG. 2 is a diagram of a reconstructed phylogenetic tree structure. The entire topology of the phylogenetic tree is reconstructed. Unknown nodes 100, 116 and 104 are reconstructed from known nodes 106, 118, 108 and 120. Reconstructing the entire topology requires the calculation to be performed from a fairly large portion of the character sequence of each known node. Examples of sequences that are used to reconstruct the topology are sequence 122 "CGCT" in node 106, sequence 124 "ACCT" in node 118, sequence 126 "ATAT" in node 108 and sequence 128 "ATTT" in node 120.

Conventionally, the number of characters in the sequence that is required to reconstruct the topology is a polynomial function of the number of known nodes. For example, if the polynomial function is $n^3$, then 64 characters in each sequence are used to reconstruct the topology from 4 known nodes because 64 is the cube of 4. In another example, 1000 characters in a sequence are used to reconstruct the topology of 10 known nodes because 1000 is the cube of 10 known nodes. The polynomial function of the number of known nodes often yields a large number. This is problematic because often a large number of characters of a sequence is not available from all of the known nodes.

After the entire topology of a phylogenetic tree is reconstructed, the characters or sequence of each of the reconstructed nodes are estimated or inferred from the topology. Conventional methods of estimating the characters include the parsimony method and the maximum-likelihood (ML) method. The ML method is based on choosing the value of an unknown parameter under which the probability of obtaining known samples is highest. Often, the topology of the phylogenetic tree is not known with a high degree of accuracy. Estimating the characters using the ML method from a less than highly accurate phylogenetic tree topology provides less than accurate characters.

For the reasons stated above, and for other reasons stated below which will become apparent to those skilled in the art upon reading and understanding the present specification, there is a need in the art for reconstructing a tree topology from a smaller portion of the data of known nodes. There is also a need for improved accuracy in estimating data of the nodes of a phylogenetic tree from a less than highly accurate phylogenetic tree topology.

SUMMARY

A tree reconstructor is described. The reconstructor allows a topology to be reconstructed from a smaller portion of samples of data of known nodes. The topology is reconstructed iteratively, for successively higher levels of a reconstructed tree topology. Excluding distant pairs of nodes in the reconstruction allows the smaller portion of samples in reconstructing local topology. In addition, using majority functions in estimating data of nodes of a phylogenetic tree allows the recursive reconstruction of data at nodes of the tree.

BRIEF DESCRIPTION OF THE DRAWINGS

FIG. 8 is a block diagram of an exemplary computer that might be programmed to perform the functions described herein.

DETAILED DESCRIPTION

Figure 1:
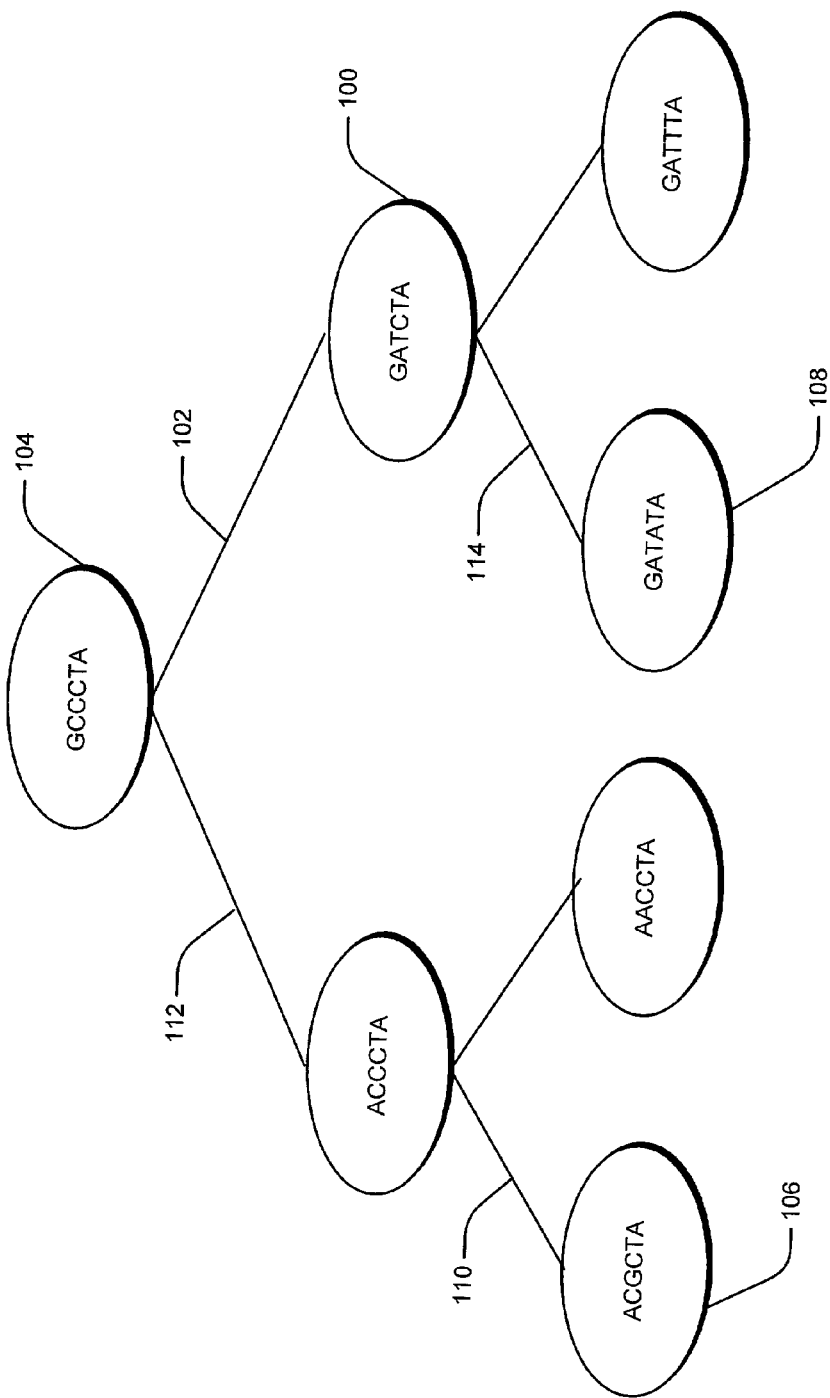
FIG. 1 is a diagram of a complete phylogenetic tree structure.
Figure 2:
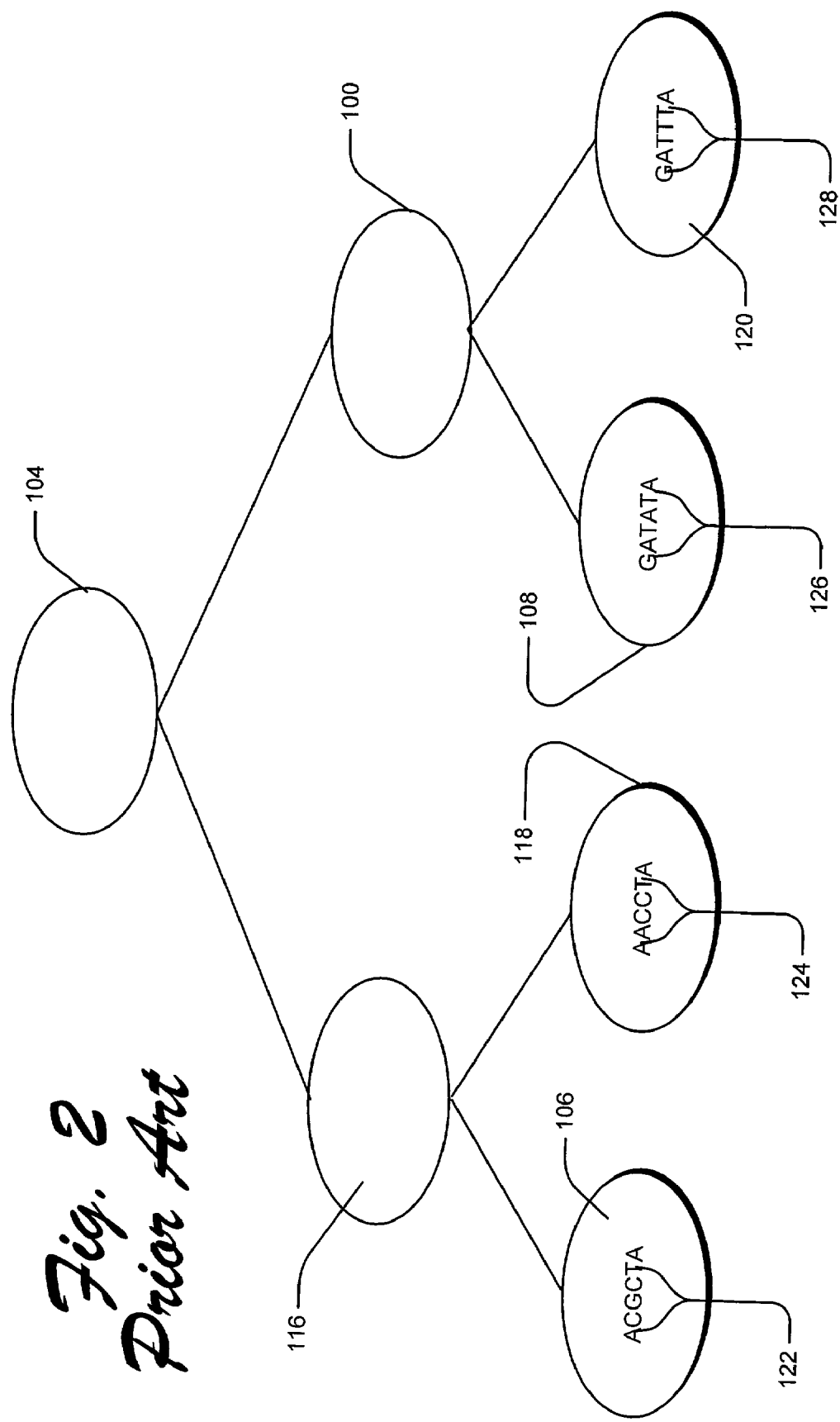
FIG. 2 is a diagram of a reconstructed phylogenetic tree structure.
Figure 3:
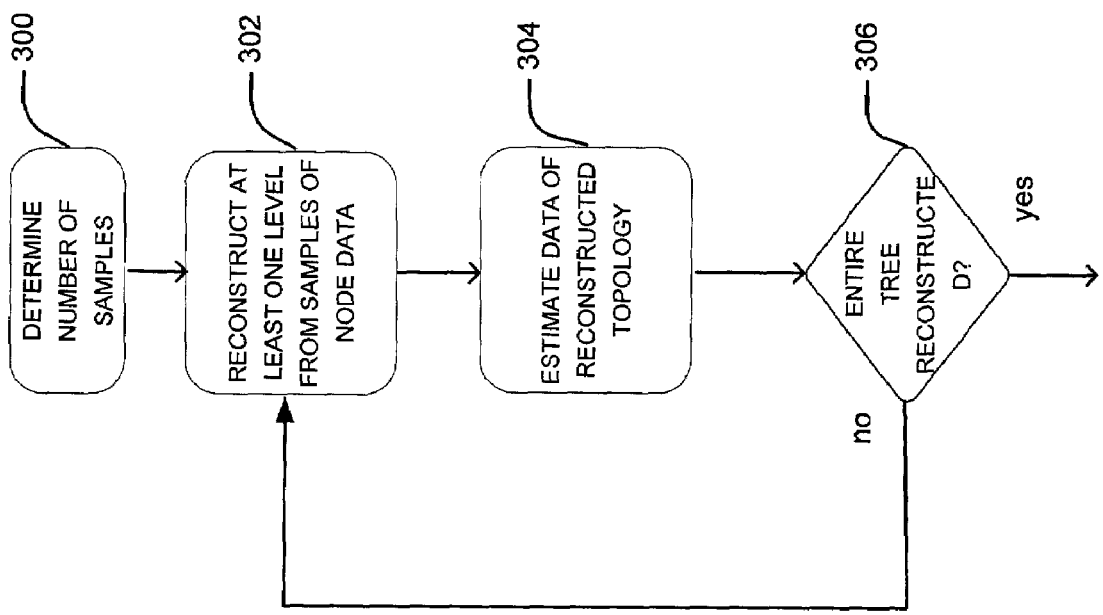
FIG. 3 illustrates a method for iteratively reconstructing an entire phylogenetic tree from a plurality of known nodes.

FIG. 3 illustrates a method for iteratively reconstructing an entire phylogenetic tree from a plurality of known nodes. The order in which the method is described is not intended to be construed as a limitation. Furthermore, the method can be implemented in any suitable hardware, software, firmware, or combination thereof.

In the method of FIG. 3, topology and node data are reconstructed iteratively, for successively higher levels of the reconstructed tree topology. Each iteration reconstructs a partial reconstructed tree topology. The method is performed until an entire tree is reconstructed. A first iteration of the method in FIG. 3 uses information from known nodes. Each subsequent iteration is performed using information that is generated from the immediately previous iteration.

A boundary is a highest level of nodes that are available to use as a basis of constructing. In the first iteration, the boundary consists of the known nodes. In subsequent iterations, the boundary is a highest level of nodes that have been reconstructed in the method in FIG. 3. Examples of the boundaries are discussed in conjunction with FIG. 4 below.

A local topology is one or more levels of nodes that are being reconstructed in a current iteration. The local topology is bounded at a lower level by the boundary. In some embodiments, the local topology includes less than all predicted levels, such as only one level of nodes, or such as a plurality of levels.

A known node is a node for which the data is known. In one scenario, the known nodes represent phylogenetic nodes. The data of each known phylogenetic node indicates a DNA sequence or sub-sequence represented by a string of characters or letters. The data is also known as a spin value. The string of characters or letters is selected from a group of characters. In some embodiments, the known nodes include known leaf nodes and known parent nodes. In other embodiments, known nodes include known leaf nodes exclusively.

At block 300, a count of samples of data is determined. The count is calculated as approximately equal to c ln(n). A natural logarithm of the number of the plurality of boundary nodes ln(n) depends on n, the number of boundary nodes. A constant factor c depends on the mutation rates and on a required confidence level. The count c ln(n) of samples results in a smaller count of samples being used than in conventional solutions. The smaller count of samples is beneficial in that reconstructing the node topology is feasible in situations where only limited samples of data is available. In reconstructing, the same samples of data are used from each of the nodes. In a phylogenetics implementation, each sample is one character, and samples are a plurality of characters.

At block 302, one or more levels of a predicted node topology are reconstructed from samples of data from each of a plurality of boundary nodes. In the first iteration, the boundary consists of the known nodes. In subsequent iterations, the boundary is a highest level of nodes that have been reconstructed in the method in FIG. 3.

In the described embodiment, each iteration of block 302 reconstructs a single level of the predicted node topology. In other embodiments, each iteration of block 302 might reconstruct more than one level, but less than all of the predicted reconstructed levels.

The same samples of characters are used from each sequence for the reconstructing at block 302. For example, for nodes that have fifty characters in each sequence, the first, tenth, twelfth, twenty-eight, and the forty-second character may be used as the samples from each sequence, for each node. The method in FIG. 5 which will be described in more detail below, is one embodiment of the reconstructing at block 302.

At block 304, data for each of the nodes reconstructed at block 302 is estimated. The estimating is performed from the level of nodes that is reconstructed in the previous iteration of block 302, and from the data of these reconstructed nodes.

In the first iteration of block 304, data for the one or more levels of the reconstructed topology is estimated from the topology of the known nodes, and from the samples of data of each of the known nodes. In subsequent iterations of block 304, data for the one or more levels of the reconstructed topology is estimated from the topology of the highest level of the constructed nodes from the previous iteration of block 302, and from the samples of data of each of the nodes at the highest level of constructed nodes from the previous iteration of block 302 and block 304.

In the case where data is estimated from only two nodes, the estimating does not provide a population size that is statistically significant enough. In these cases, data is estimated from the next lowest level of the topology that has more than two nodes.

After the nodes of one set of levels have been reconstructed in block 302 and data has been estimated in block 304, a determination of whether or not the entire predicted tree has been reconstructed is made in block 306. One indication that reconstruction of the entire predicted tree is complete is that the topology of the highest level of the constructed nodes from the previous iteration of block 302 has only one node, a root node. If the entire predicted tree has not been reconstructed, then the method is reiterated starting at block 302. If the entire predicted tree has been reconstructed, then the method ends.

In one embodiment of the estimating at block 304, a majority function is implemented. The majority function is a logic function from n inputs to one output, defined as follows: If more inputs are TRUE than are FALSE, then the majority function returns TRUE. Otherwise, the function returns FALSE. Using majority functions in estimating data of nodes of a phylogenetic tree allows the recursive reconstruction of data at nodes of the tree.

When the inputs to the majority function have more than two values, the majority outputs the most frequent value amongst the input values. Both in the binary and non-binary case, ties are decided randomly. So if the two most frequent inputs appear exactly the same number of times, then with probability ½ the output will be the first, and with probability ½ the second"

The majority function Maj:$\{-1,1\}^d \to \{-1,1\}$ be defined as:

$$Maj(x_1, \ldots, x_d) = \text{sign}\left(\sum_{i=1}^{d} x_i + 0.5\omega\right),$$

where $\omega$ is an unbiased ±1 variable which is independent of the $x_i$. Thus when d is odd, $$Maj(x_1, \ldots, x_d) = \text{sign}\left(\sum_{i=1}^{d} x_i\right).$$

When d is even, $$Maj(x_1, \ldots, x_d) = \text{sign}\left(\sum_{i=1}^{d} x_i\right), \text{ unless } \sum_{i=1}^{d} x_i = 0,$$

in which case Maj($x_1, \ldots, x_d$) is chosen to be ±1 with probability ½. The difference between the odd and even case is the case in which $$\sum_{i=1}^{d} x_i = 0,$$

which applies only for the even case.

In varying embodiments, the stochastic mutation model may be selected from the Cavender, Farris and Neyman (CFN) model, or the Kimura 2-parameter model, or the Kimura 3-parameter model. Any symmetric stochastic mutation model can be used with the majority function. Aspects of the method in FIG. 3 can be combined with other aspects of reconstructing, as will be described below with reference FIG. 7.

Figure 4:
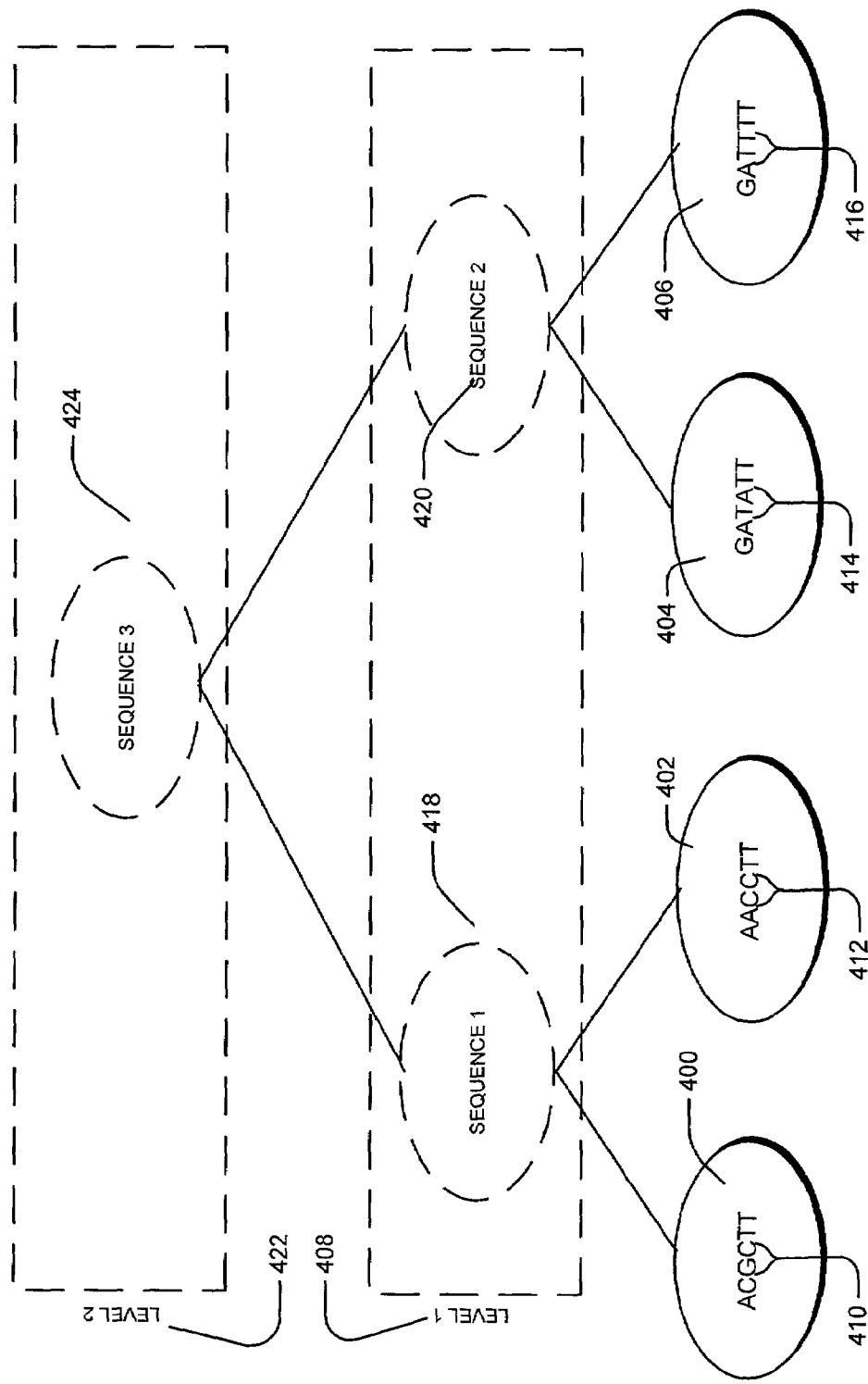
FIG. 4 is a diagram of a phylogenetic tree structure that is iteratively reconstructed in accordance with the method of FIG. 3.

FIG. 4 is a diagram of a phylogenetic tree structure that is iteratively reconstructed in accordance with the method of FIG. 3. The phylogenetic tree structure is reconstructed from known nodes. The known nodes 400, 402, 404, and 406 include data "ACGCTT," "AACCTT," "GATATT," and "GATTTT" respectively.

In a first iteration of the method of FIG. 3, a boundary is a level of nodes of the known nodes 400, 402, 404, and 406. A first level LEVEL1 408 of a predicted node topology is reconstructed from samples of data "GC" 410, "CC" 412, "TA" 414, and "TT" 416 from each of the boundary nodes, 400, 402, 404, and 406, respectively. The first level LEVEL1 408 of reconstructed topology includes nodes 418 and 420. LEVEL1 408 is an example of a local topology.

In FIG. 4, the samples of characters are contiguous characters. However, in other embodiments, the samples are selected at random. In still other embodiments, the samples are selected with a purpose.

In reconstructing, the same samples are used from each of the nodes, as discussed above. Thus, the count of samples is uniform for each node. The size is approximately equal to a factor of a natural logarithm of the number of the plurality of known nodes. For example where the number of known nodes is 4, and the factor is approximately 1.443, the count of the samples is approximately (1.443)*ln(4), which is approximately 2.0. Thus, in FIG. 4, the samples of data 410, 412, 414, and 416 are two characters each, "GC," "CC," "GC," and "CC," respectively. Using a sample count that is calculated in reference to a natural logarithm of the number of the plurality of known nodes results in a smaller number of samples being used than in conventional solutions, which allows reconstruction in situations where only limited samples of data are available.

In contrast, conventional reconstruction of phylogenetic trees uses a larger number of sample characters. For example, where the number of characters in the sequence that is required to reconstruct the topology is a polynomial function $n^3$ of the number of known nodes, then 64 characters in each sequence are used to reconstruct the topology from 4 known nodes because 64 is the cube of 4. The sixty-four sample characters used in conventional reconstruction of phylogenetic trees is significantly more than the four sample characters used in FIG. 4.

In the first iteration of the method of FIG. 3, data for the first level LEVEL1 408 of the reconstructed topology is estimated from the topology of the boundary of known nodes, and from the samples of data of each of the known nodes. The estimated data in nodes 418 and 420 are SEQUENCE1 and SEQUENCE2, respectively. In a phylogenetic application, sequences such as "ACGCTT," "AACCTT," "GATATT," and "GATTTT" in known nodes 400, 402, 404, and 406, respectively, and such as SEQUENCE1 and SEQUENCE2 in reconstructed nodes 418 and 420, are represented by a string of characters selected from a group comprising the characters, "A," "C," "G" and "T."

In a second iteration of the method, the boundary is a highest level of constructed nodes from the previous iteration of the method, nodes 418 and 420. A second level LEVEL2 422 of the predicted node topology is reconstructed from samples of data from each of the boundary nodes, 418 and 420. The second level LEVEL2 422 of reconstructed topology includes node 424. LEVEL2 422 is an example of a local topology.

Data for the second level LEVEL2 422 of the reconstructed topology is estimated from the topology of the boundary nodes, 418 and 420 and from the samples of data of each of the boundary nodes. The estimated data in node 424 is SEQUENCE3. In other embodiments, a plurality of levels may be reconstructed in each iteration, and data for the node of the reconstructed levels estimated in each iteration.

Iteration ends when the entire tree is complete. The entire tree is complete when a topology level having only one node, a root node such as node 424, is reconstructed and data is estimated for the one node. In this way, starting with samples of data from known nodes 400, 402, 404, and 406, a tree topology is reconstructed in levels LEVEL1 408 and LEVEL2 422, and data are estimated for the nodes 418, 420, and 424 of the constructed tree. The reconstructing and estimating is performed in iterative levels.

Figure 5:
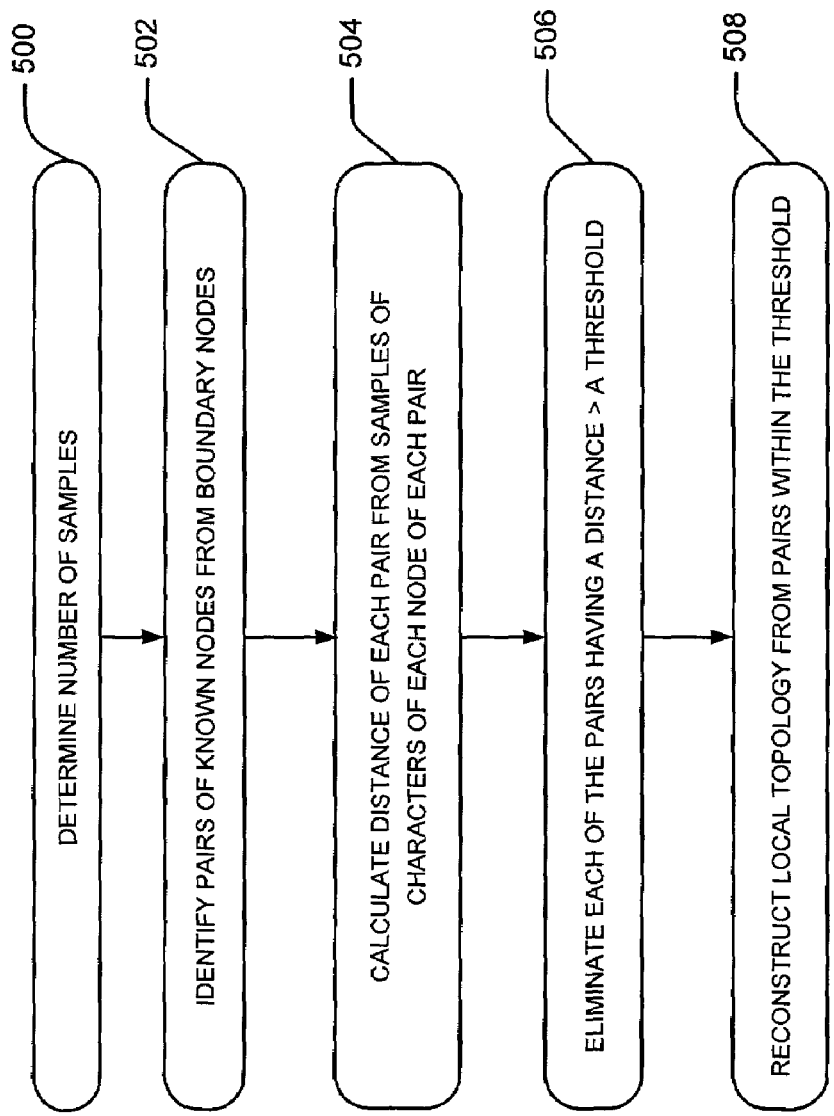
FIG. 5 illustrates a method for reconstructing a predicted topology from a plurality of closely-correlated nodes.

FIG. 5 illustrates a method for reconstructing a predicted topology from a plurality of closely-correlated nodes. The method in FIG. 5 is one embodiment of the reconstructing in action 302 in FIG. 3. The order in which the method is described is not intended to be construed as a limitation. Furthermore, the method can be implemented in any suitable hardware, software, firmware, or combination thereof.

In block 500, a count of samples of data is determined as approximately equal to c ln(n), as discussed above. This smaller count of samples allows reconstructing a node topology in situations where only limited samples of data is available.

In block 502, one or more pairs of a plurality of nodes are identified from a boundary of nodes. In an embodiment of block 502, in a first iteration of an iterative reconstruction of a predicted tree structure, the boundary comprises the plurality of known nodes. Thus, in the first iteration, one or more pairs of a plurality of nodes are identified from the plurality of known nodes. In subsequent iterations, the boundary is a plurality of reconstructed nodes from the immediately previous iteration. Thus, in subsequent iterations, one or more pairs of nodes are identified from a plurality of reconstructed nodes from the immediately previous iteration.

In block 504, a distance is calculated for each of the one or more identified pairs from the samples of data of the one or more identified pairs. The distance is calculated as a measure of correlation. The pairwise distances are defined as $D^*(u,v) = -\log_+ c(u,v)$ where $$c(u, v) = \frac{1}{k} \sum_{t=1}^{k} \sigma_u^t \sigma_v^t$$

is the correlation between the data at node u and node v. So if the data at nodes u and v is identical, then $c(u, v)=1$ and therefore $D^*(u, v)=0$. If, on the other hand, the sequences at u and v are uncorrelated we expect that $c(u, v)$ will be close to 0 and therefore that $D^*(u, v)$ will be very large.

In block 506, one or more of the identified pairs of the plurality of known nodes that are within a predetermined threshold distance are selected. The selecting eliminates pairs having a distance that are not closely-correlated.

The threshold is set or determined before the beginning of the method in reference to an application, such as phylogenetics or computer network analysis. In an example from network analysis, leaf nodes represent end-users. Furthermore, to learn the tree network connecting groups of end users, broadcasted information from a central site to all nodes is tested, assuming that the data collected by the different end users may be sent without error and processed at a single node.

In block 508, one or more levels of nodes of tree topology are reconstructed from the samples of data of the selected pairs of nodes. The reconstructed tree topology has one or more reconstructed nodes. The topology of T is determined from the closely-correlated pairwise distances $D^*(u,v) = -\log_+ c(u,v)$ in action 504.

In some embodiments, a four-point function is used for reconstruction. We apply a four-point function to examine all 4 nodes $u_1$, $u_2$, $u_3$ and $u_4$ such that all of their pairwise distances are within the threshold. For each 4-tuple $u_1, u_2, u_3$ and $u_4$ we determine the relationship between the 4 nodes. A determination is made as to whether the 4 nodes related by a tree structure where $u_1$ and $u_2$ have a common ancestor which is related to the common ancestor of $u_3$ and $u_4$, or is the right pairing $(u_1, u_3)$ with $(u_2, u_4)$, or maybe $(u_1, u_4)$ with $(u_2, u_3)$. In the first case, it is expected that $D(u_1,u_3)+D(u_2,u_4)=D(u_1,u_4)+D(u_2,u_3)$ and that this quantity is smaller than $D(u_1, u_2)+D(u_3, u_4)$. Similarly for other cases. These inequalities should approximately hold for $D^*$. Given all the pairing for all 4-tuples, we can declare u and v sisters if they were paired together for all the 4-tuples containing u and v. Thus we can reconstruct one level of the topology. Similarly we can reconstruct further levels. A four-point function examines four nodes.

Reconstructing a topology from closely correlated pairs of nodes allows a higher degree of accuracy in the reconstruction. Alternatively, the topology is reconstructed from a smaller count of samples of the node data. Aspects of the method of FIG. 5 may be combined with other aspects of reconstructing, as will be described below with reference FIG. 7.

Figure 6:
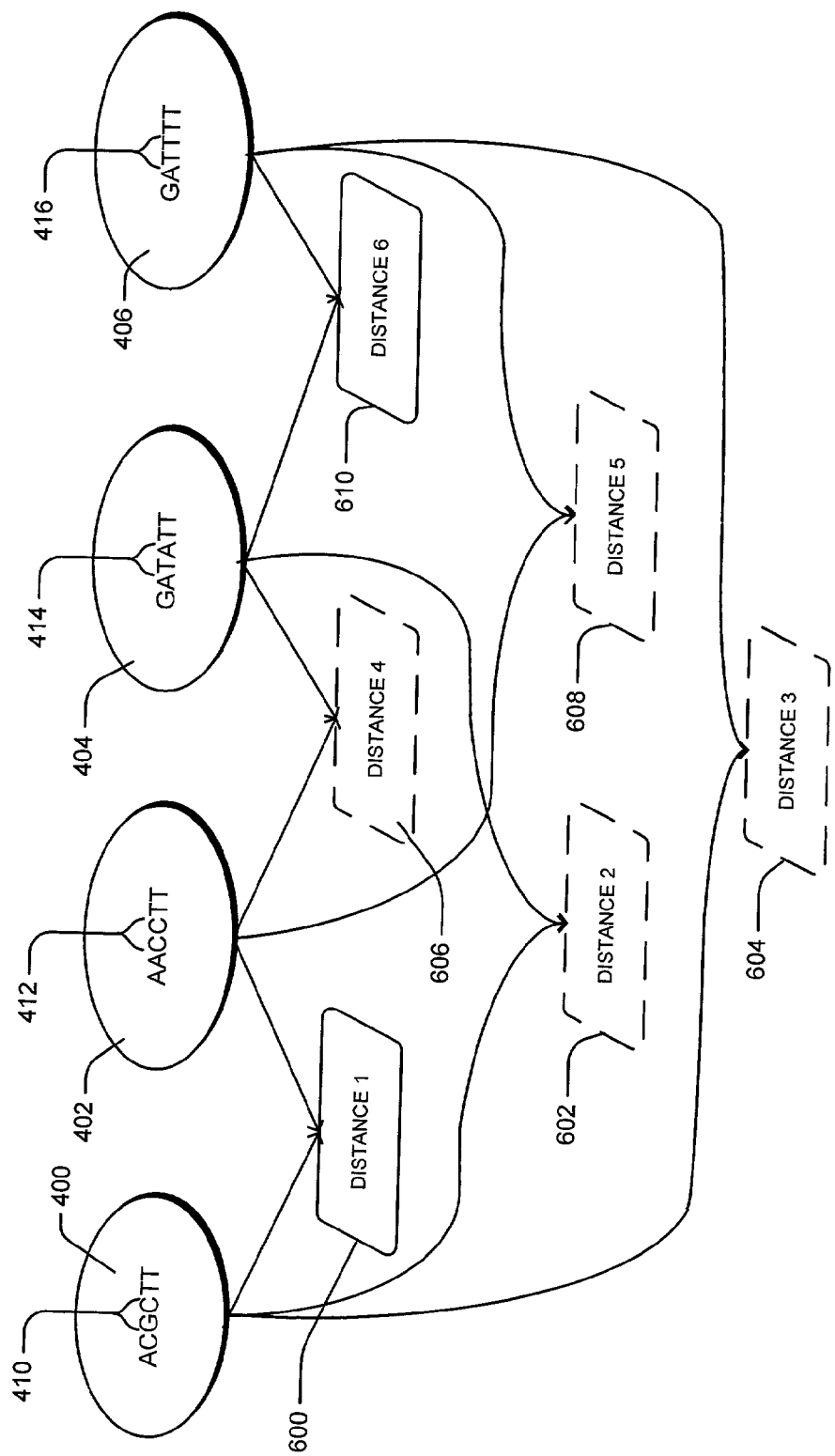
FIG. 6 is a diagram of data structures that are involved in reconstruction of a phylogenetic tree in accordance with the method of FIG. 5.

FIG. 6 is a diagram of data structures that are involved in reconstruction of a phylogenetic tree topology in accordance with the method of FIG. 5. More specifically, FIG. 6 illustrates data structures that are involved in reconstruction of the first reconstructed level LEVEL1 408 in FIG. 4. The phylogenetic tree structure is reconstructed from a plurality of closely-correlated nodes.

Pairs of nodes are identified from samples of data of the nodes, as in block 502 in FIG. 5. Each unique combination of pairs is identified. Possible combinations of pairs in FIG. 6 are (400, 402), (400, 404), (400, 406), (402, 404), (402, 406), and (404, 406).

The distance between each node is calculated. The distance is calculated using $D^*(u,v) = -\log_+ c(u,v)$ as in block 504 in FIG. 5. In FIG. 6, the distances for node pairs (400, 402), (400, 404), (400, 406), (402, 404), (402, 406), (404, 406) are represented by distance pairs DISTANCE1 600, DISTANCE2 602, DISTANCE3 604, DISTANCE4 606, DISTANCE5 608, and DISTANCE6 610, respectively.

The pairs having a distance greater than a predetermined threshold are eliminated from further use in the reconstruction, as in block 506 in FIG. 5. The distance is determined from the characters of each node of each pair. In this case, the threshold is 2. In FIG. 6, pairs having a distance of greater than 2 are eliminated. In FIG. 6, only pairs (400, 402) having a distance represented by DISTANCE1 600 and (404, 406) having a distance represented by DISTANCE6 610 are within a distance of 2. Thus, pairs (400, 404), (400, 406), (402, 404), and (402, 406) having distances that represented by DISTANCE2 602, DISTANCE3 604, DISTANCE4 606, and DISTANCE5 608, respectively are eliminated, leaving only pairs (400, 402) represented by DISTANCE1 600 and (404, 406) represented by DISTANCE6 610 for use in reconstruction. Reconstruction is performed as in block 508 in FIG. 5 from distance pairs DISTANCE1 600 and DISTANCE6 610 that are within the threshold distance of 2.

Figure 7:
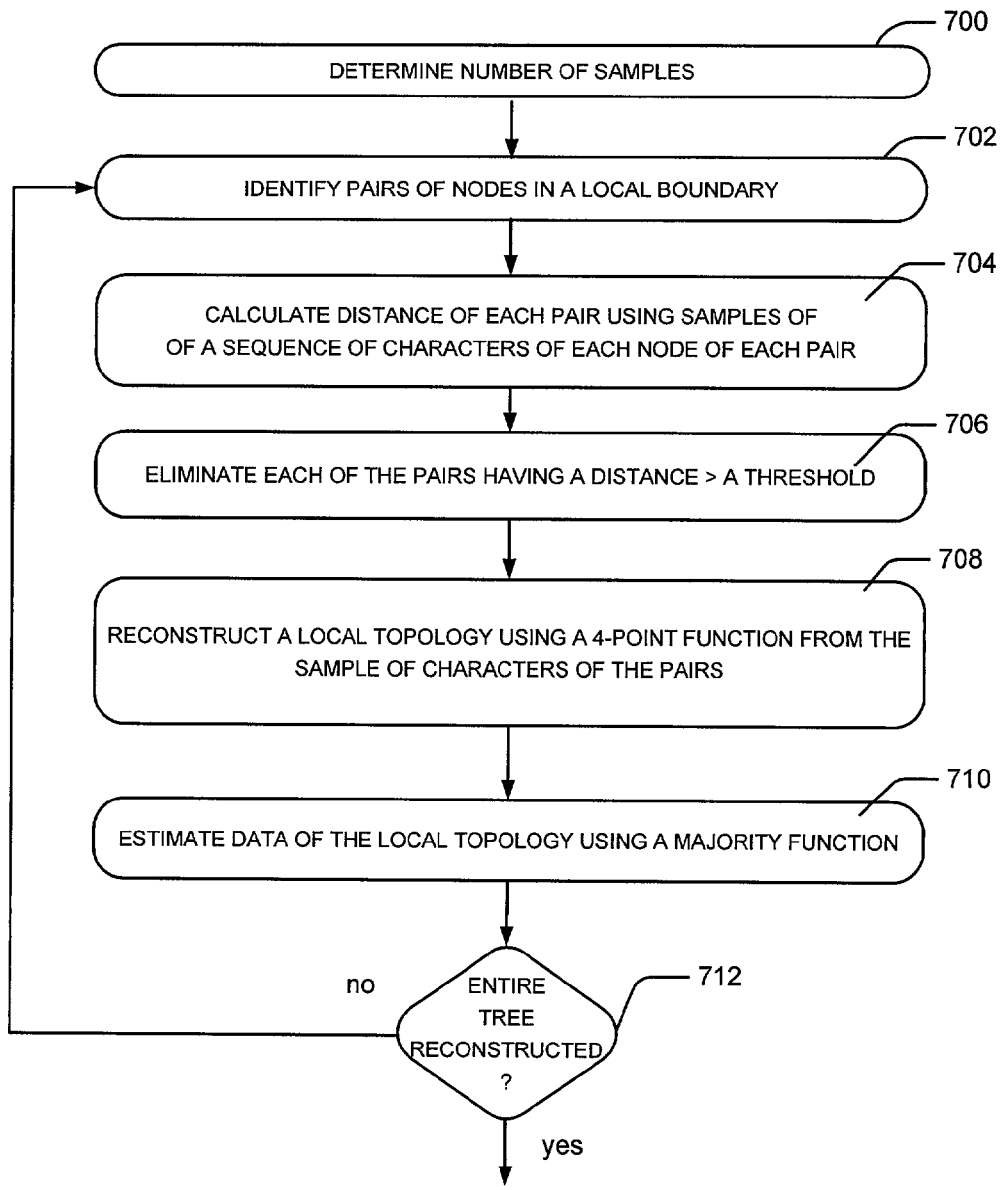
FIG. 7 illustrates a method for reconstructing a predicted phylogenetic tree.

FIG. 7 illustrates a method for reconstructing a predicted phylogenetic tree. The order in which the method is described is not intended to be construed as a limitation. Furthermore, the method can be implemented in any suitable hardware, software, firmware, or combination thereof.

In block 700, a count of samples of data is determined as approximately equal to c ln(n), as discussed above. This smaller count of samples allows reconstructing a node topology in situations where only limited samples of data is available.

At block 702, pairs of known nodes are identified. The pairs of known nodes are identified from the sequence of characters of the pairs of a local boundary. In the first performance of block 702, the local boundary is a set of known nodes. Subsequently, the local boundary is a highest level of reconstructed and estimated nodes.

In block 704, a distance of each pair is calculated from the samples of the sequence of characters of each node of each pair. In block 706, each of the pairs having a distance that is greater than a threshold are eliminated or excluded from the pairs.

In block 708, a local topology having one or more levels of nodes is reconstructed using a 4-point function from the samples of the sequence of characters of the pairs, as discussed above.

In block 710, a sequence of characters of each of the one or more nodes in OF the reconstructed phylogenetic tree topology is estimated in accordance with a stochastic mutation model using a majority function.

At block 712, when an entire tree is determined to be reconstructed, the method ends, otherwise the method continues at block 700.

FIG. 8 is a block diagram of an exemplary computer that might be programmed to perform the functions described herein. The various components and functionality described above are implemented with individual computers. FIG. 8 shows components of typical example of such a computer, referred by to reference numeral 80. The components shown in FIG. 8 are only examples, and are not intended to suggest any limitation as to the scope of the functionality of the invention; the invention is not necessarily dependent on the features shown in FIG. 8.

Generally, various different general purpose or special purpose computing system configurations can be used. Examples of well known computing systems, environments, and/or configurations that may be suitable for use with the invention include, but are not limited to, personal computers, server computers, hand-held or laptop devices, multi-processor systems, microprocessor-based systems, set top boxes, programmable consumer electronics, network PCs, minicomputers, mainframe computers distributed computing environments that include any of the above systems or devices, and the like.

The functionality of the computers is embodied in many cases by computer-executable instructions, such as program modules, that are executed by the computers. Generally, program modules include routines, programs, objects, components, data structures, etc. that perform particular tasks or implement particular abstract data types. Tasks might also be performed by remote processing devices that are linked through a communications network. In a distributed computing environment, program modules may be located in both local and remote computer storage media.

The instructions and/or program modules are stored at different times in the various computer-readable media that are either part of the computer or that can be read by the computer. Programs are typically distributed, for example, on floppy disks, CD-ROMs, DVD, or some form of communication media such as a modulated signal. From there, they are installed or loaded into the secondary memory of a computer. At execution, they are loaded at least partially into the computer's primary electronic memory. The invention described herein includes these and other various types of computer-readable media when such media contain instructions, programs, and/or modules for implementing the steps and actions described above in conjunction with microprocessors or other data processors. The invention also includes the computer itself when programmed according to the methods and techniques described above.

For purposes of illustration, programs and other executable program components such as the operating system are illustrated herein as discrete blocks, although it is recognized that such programs and components reside at various times in different storage components of the computer, and are executed by the data processor(s) of the computer.

With reference to FIG. 8, the components of computer 800 may include, but are not limited to, a processing unit 820, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISAA) bus, Video Electronics Standards Association (VESA) local bus, and Peripheral Component Interconnect (PCI) bus also known as the Mezzanine bus.

Computer 800 typically includes a variety of computer-readable media. Computer-readable media can be any available media that can be accessed by computer 800 and includes both volatile and nonvolatile media, removable and non-removable media. By way of example, and not limitation, computer-readable media may comprise computer storage media and communication media. Computer storage media include both volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media typically embodies computer-readable instructions, data structures, program modules or other data in a modulated data signal such as a carrier wave or other transport mechanism and includes any information delivery media. The term "modulated data signal" means a signal that has one or more if its characteristics set or changed in such a manner as to encode information in the signal. By way of example, and not limitation, communication media includes wired media such as a wired network or direct-wired connection and wireless media such as acoustic, RF, infrared and other wireless media. Combinations of any of the above should also be included within the scope of computer readable media.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 800, such as during start-up, is typically stored in ROM 831. RAM 832 typically contains data and/or program modules that are immediately accessible to and/or presently being operated on by processing unit 820. By way of example, and not limitation, FIG. 8 illustrates operating system 834, application programs 835, other program modules 836, and program data 837.

The computer 800 may also include other removable/non-removable, volatile/nonvolatile computer storage media. By way of example only, FIG. 8 illustrates a hard disk drive 841 that reads from or writes to non-removable, nonvolatile magnetic media, a magnetic disk drive 851 that reads from or writes to a removable, nonvolatile magnetic disk 852, and an optical disk drive 855 that reads from or writes to a removable, nonvolatile optical disk 856 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 841 is typically connected to the system bus 821 through a non-removable memory interface such as interface 840, and magnetic disk drive 851 and optical disk drive 855 are typically connected to the system bus 821 by a removable memory interface such as interface 850.

The drives and their associated computer storage media discussed above and illustrated in FIG. 8 provide storage of computer-readable instructions, data structures, program modules, and other data for computer 800. In FIG. 8, for example, hard disk drive 841 is illustrated as storing operating system 844, application programs 845, other program modules 846, and program data 847. Note that these components can either be the same as or different from operating system 834, application programs 835, other program modules 836, and program data 837. Operating system 844, application programs 845, other program modules 846, and program data 847 are given different numbers here to illustrate that, at a minimum, they are different copies. A user may enter commands and information into the computer 800 through input devices such as a keyboard 862 and pointing device 861, commonly referred to as a mouse, trackball, or touch pad. Other input devices (not shown) may include a microphone, joystick, game pad, satellite dish, scanner, or the like. These and other input devices are often connected to the processing unit 820 through a user input interface 860 that is coupled to the system bus, but may be connected by other interface and bus structures, such as a parallel port, game port, or a universal serial bus (USB). A monitor 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer may operate in a networked environment using logical connections to one or more remote computers, such as a remote computer 880. The remote computer 880 may be a personal computer, a server, a router, a network PC, a peer device or other common network node, and typically includes many or all of the elements described above relative to computer 800, although only a memory storage device 881 has been illustrated in FIG. 8. The logical connections depicted in FIG. 8 include a local area network (LAN) 871 and a wide area network (WAN) 873, but may also include other networks. Such networking environments are commonplace in offices, enterprise-wide computer networks, intranets, and the Internet.

When used in a LAN networking environment, the computer 800 is connected to the LAN 871 through a network interface or adapter 870. When used in a WAN networking environment, the computer 800 typically includes a modem 872 or other means for establishing communications over the WAN 873, such as the Internet. The modem 872, which may be internal or external, may be connected to the system bus 821 via the user input interface 860, or other appropriate mechanism. In a networked environment, program modules depicted relative to the computer 800, or portions thereof, may be stored in the remote memory storage device. By way of example, and not limitation, FIG. 8 illustrates remote application programs 885 as residing on memory device 881. It will be appreciated that the network connections shown are exemplary and other means of establishing a communications link between the computers may be used.

Although details of specific implementations and embodiments are described above, such details are intended to satisfy statutory disclosure obligations rather than to limit the scope of the following claims. Thus, the invention as defined by the claims is not limited to the specific features described above. Rather, the invention is claimed in any of its forms or modifications that fall within the proper scope of the appended claims, appropriately interpreted in accordance with the doctrine of equivalents.

Although the systems and methods have been described in language specific to structural features and/or methodological steps, it is to be understood that the invention defined in the appended claims is not necessarily limited to the specific features or steps described. Rather, the specific features and steps are disclosed as preferred forms of implementing the claimed invention.

The invention claimed is:

1. One or more computer-readable media comprising computer executable instructions that, when executed, direct a computing system to perform a method comprising:
   reconstructing a predicted phylogenetic tree topology by:
      determining samples of characters of a plurality of known nodes;
      identifying each of the samples including a number of characters;
      calculating the number of characters being approximately equal to a factor of a natural logarithm of the number of the plurality of known nodes,
      selecting one or more of the plurality of known nodes that are within a predetermined threshold;
      yielding a reconstructed phylogenetic tree topology having one or more reconstructed nodes based on the selecting one or more of the plurality of known nodes;
   estimating a sequence of characters of each of the one or more nodes in the reconstructed phylogenetic tree topology in accordance with a stochastic mutation model using a majority function;
   presenting the reconstructed predicted phylogenetic tree topology; and
   determining closeness of relationship between species or individuals, based on the reconstructed phylogenetic tree topology.

2. The computer-readable media as recited in claim 1, wherein the stochastic mutation model farther comprises a Cavender, Farris and Neyman model.

3. The computer-readable media as recited in claim 1, wherein the stochastic mutation model further comprises a Kimura 2-parameter model.

4. The computer-readable media as recited in claim 1, wherein the stochastic mutation model further comprises a Kimura 3-parameter model.

5. The computer-readable media as recited in claim 1, wherein the plurality of known nodes further comprise a plurality of known leaf nodes.

6. The computer-readable media as recited in claim 1, wherein the plurality of known nodes farther comprise a plurality of known exclusive leaf nodes.

7. The computer-readable media as recited in claim 1, wherein the reconstructing further comprises using a four-point function from the samples of the characters of the plurality of known nodes.

8. The computer-readable media as recited in claim 1, wherein the reconstructing further comprises:
   identifying one or more pairs of the plurality of known nodes from the samples of characters of the plurality of known nodes;

calculating a distance for each of the one or more identified pairs of the plurality of known nodes from the samples of characters of the one or more identified pairs;

selecting one or more of the identified pairs of the plurality of known nodes that are within a predetermined threshold distance; and wherein the reconstructing is based on the samples of characters of the selected pairs of known nodes.

9. The computer-readable media as recited in claim 1, further comprising:

performing the reconstructing and the estimating iteratively until an entire tree topology is reconstructed.

10. The computer-readable media as recited in claim 1, wherein:

the reconstructing further comprises reconstructing a first portion of the predicted phylogenetic tree topology having one or more nodes;

the estimating further comprises estimating characters of each of the one or more nodes in the first portion of the predicted phylogenetic tree topology, and the method further comprises:

reconstructing one or more levels of the predicted phylogenetic tree topology from samples of the characters of the first portion of the predicted phylogenetic tree topology, wherein the partial tree topology further comprises a second portion of the predicted tree topology having one or more nodes; and estimating characters of each of the one or more nodes in the second portion of the predicted tree topology.

11. A computer-based method of reconstructing an entire phylogenetic tree from a plurality of known leaf nodes of the phylogenetic tree, the method comprising:

reconstructing one or more levels of a predicted phylogenetic tree topology from samples of characters of the plurality of known leaf nodes by:

determining the samples including a number of characters, calculating the number of characters being approximately equal to a factor of a natural logarithm of the number of the plurality of known leaf nodes, selecting one or more known leaf nodes that are within a predetermined threshold;

yielding a reconstructed partial phylogenetic tree topology having at least one leaf node based on the selecting one or more known leaf nodes;

estimating characters of each of the at least one leaf node in the reconstructed partial phylogenetic tree topology in accordance with a stochastic mutation model;

performing the reconstructing and the estimating iteratively to reconstruct node topology and estimate node characters for successively higher levels of the predicted phylogenetic tree topology until the entire phylogenetic tree is reconstructed;

presenting the reconstructed predicted phylogenetic tree; and determining closeness of relationship between species or individuals, based on the reconstructed phylogenetic tree.

12. The method as recited in claim 11, wherein:

the reconstructing further comprises reconstructing a first portion of the predicted phylogenetic tree topology having one or more nodes;

the estimating further comprises estimating characters of each of the one or more nodes in the first portion of the predicted phylogenetic tree topology, and the method further comprises:

reconstructing one or more levels of the predicted phylogenetic tree topology from samples of the characters of the first portion of the predicted phylogenetic tree topology, wherein the partial tree topology further comprises a second portion of the predicted tree topology having one or more nodes; and estimating characters of each of the one or more nodes in the second portion of the predicted tree topology.

13. The method as recited in claim 11, wherein the reconstructing further comprises:

identifying one or more pairs of the plurality of known leaf nodes from the samples of characters of the plurality of known leaf nodes;

calculating a distance for each of the one or more identified pairs of the plurality of known leaf nodes from the samples of characters of each of the one or more identified pairs;

selecting one or more of the identified pairs of the plurality of known leaf nodes that are within a predetermined threshold distance; and reconstructing one or more levels of the predicted tree topology from the samples of the characters of the selected pairs of known leaf nodes.

14. The method as recited in claim 11, wherein estimating the characters further comprises:

estimating the characters using a majority function.

15. A computer-based method of reconstructing an entire phylogenetic tree from a plurality of known leaf nodes of the phylogenetic tree, the method comprising:

reconstructing one or more levels of a predicted phylogenetic tree from samples of characters of the plurality of known leaf nodes;

identifying one or more pairs of the plurality of known leaf nodes from samples of characters of each of the plurality of known leaf nodes, wherein each of the samples include a number of characters, calculating the number of characters being approximately equal to a factor of a natural logarithm of the number of the plurality of known leaf nodes;

calculating a distance for each of the one or more identified pairs of the plurality of known leaf nodes from the samples of characters of the one or more identified pairs;

selecting one or more of the identified pairs of the plurality of known leaf nodes that are within a predetermined threshold distance;

yielding one or more levels of a reconstructed predicted phylogenetic tree topology from the samples of the characters of the selected pairs of known leaf nodes, the reconstructed phylogenetic tree structure having at least one node;

estimating characters of each of the at least one node in the reconstructed phylogenetic tree topology;

performing the reconstructing and the estimating iteratively to reconstruct node topology and estimate node characters for successively higher levels of the reconstructed tree topology until the entire phylogenetic tree is reconstructed;

presenting the reconstructed tree topology to an end-user; and determining closeness of relationship between species or individuals, based on the reconstructed phylogenetic tree topology.

16. The method as recited in claim 15, wherein the reconstructing further comprises:

using a four-point function from samples of the characters of the plurality of known leaf nodes.

17. The method as recited in claim 15, wherein the reconstructing further comprises:
reconstructing one or more levels of the predicted phylogenetic tree topology, yielding a reconstructed partial phylogenetic tree topology.

18. The method as recited in claim 15 wherein the estimating further comprises:
estimating the characters using a majority function.

19. A computer-based method of reconstructing a tree from a plurality of known leaf nodes of the phylogenetic tree, each known node having characters, the method comprising:
reconstructing a predicted phylogenetic tree topology from samples of the characters of each of the plurality of known leaf nodes by,
identifying each of the samples including a number of characters;
calculating the number of characters being approximately equal to a factor of a natural logarithm of the number of the plurality of known leaf nodes;
selecting one or more known leaf nodes that are within a predetermined threshold;
yielding a reconstructed phylogenetic tree topology having one or more nodes;
estimating a sequence of characters of each of the one or more nodes in the reconstructed phylogenetic tree topology in accordance with a stochastic mutation model using a majority function;
presenting the reconstructed predicted phylogenetic tree; and
determining closeness of relationship between species or individuals, based on the reconstructed phylogenetic tree topology.

20. The method as recited in claim 19, wherein the stochastic mutation model further comprises a Cavender, Farris and Neyman model.

21. The method as recited in claim 19, wherein the reconstructing further comprises:
identifying one or more pairs of the plurality of known leaf nodes from the samples of characters of the plurality of known leaf nodes;
calculating a distance for each of the one or more identified pairs of the plurality of known leaf nodes from the samples of characters of the one or more identified pairs of the plurality of known leaf nodes;
selecting one or more of the identified pairs of the plurality of known leaf nodes that are within a predetermined threshold distance; and
reconstructing one or more levels of the predicted tree topology from the samples of the characters of the selected pairs of known leaf nodes.

22. The computer-readable media as recited in claim 19, further comprising:
performing the reconstructing and the estimating iteratively until an entire tree topology is reconstructed.

23. A system to reconstruct an entire tree from a plurality of known leaf nodes of the tree:
a processor; and
a memory to store the plurality of known leaf nodes of the phylogenetic tree, each known leaf node having characters, and the memory containing instructions that causes the processor to perform actions comprising:
reconstructing one or more levels of a predicted phylogenetic tree topology from samples of the characters of each of the plurality of known leaf nodes by:
identifying each of the samples including a number of characters;
calculating the number of characters being approximately equal to a factor of a natural logarithm of the number of the plurality of known nodes;
yielding a reconstructed partial phylogenetic tree topology having at least one leaf node; and
estimating characters of each of the at least one leaf node in the reconstructed partial phylogenetic tree topology in accordance with a stochastic mutation model;
performing the reconstructing and the estimating iteratively to reconstruct node topology and estimate node characters for successively higher levels of the reconstructed tree topology until the entire phylogenetic tree is reconstructed; and
a display device to present the reconstructed predicted phylogenetic tree in determining closeness of relationship between species or individuals, based on the reconstructed phylogenetic tree topology.

24. The system as recited in claim 23, wherein:
the reconstructing further comprises reconstructing a first portion of the predicted phylogenetic tree topology having one or more nodes;
the estimating further comprises estimating characters of each of the one or more nodes in the first portion of the predicted phylogenetic tree topology, and
the memory further comprises instructions that causes the processor to perform actions comprising:
reconstructing one or more levels of the predicted phylogenetic tree topology from samples of the characters of the first portion of the predicted phylogenetic tree topology, wherein the partial tree topology further comprises a second portion of the predicted tree topology having one or more nodes; and
estimating characters of each of the one or more nodes in the second portion of the predicted tree topology.

25. The system as recited in claim 23, wherein the reconstructing further comprises:
identifying one or more pairs of the plurality of known leaf nodes from the samples of characters of the plurality of known leaf nodes;
calculating a distance for each of the one or more identified pairs of the plurality of known leaf nodes from the samples of characters of the one or more identified pairs;
selecting one or more of the identified pairs of the plurality of known leaf nodes that are within a predetermined threshold distance; and
reconstructing one or more levels of the predicted tree topology from the samples of the characters of the selected pairs of known leaf nodes.

26. The system as recited in claim 23, wherein estimating the characters further comprises:
estimating the characters using a majority function.

27. A system to reconstruct an entire phylogenetic tree from a plurality of known leaf nodes of the tree:
a processor; and
a memory to store the plurality of known leaf nodes of the phylogenetic tree, each known leaf node having characters, and containing instructions that causes the processor to perform actions comprising:
reconstructing one or more levels of a phylogenetic tree topology from samples of the characters of the plurality of known leaf nodes by:
identifying one or more pairs of the plurality of known leaf nodes from samples of the characters, the samples including a number of characters;

calculating the number of characters being approximately equal to a factor of a natural logarithm of the number of the plurality of known leaf nodes;

calculating a distance for each of the one or more identified pairs from the samples of characters of the one or more identified pairs;

selecting one or more identified pairs that are within a predetermined threshold distance; and yielding a reconstructed predicted phylogenetic tree topology from samples of the characters of the one or more selected pairs;

estimating characters of each of the reconstructed nodes in the reconstructed phylogenetic tree topology in accordance with a stochastic mutation model;

performing the reconstructing and the estimating iteratively to reconstruct node topology and estimate node characters for successively higher levels of the reconstructed tree topology until the entire phylogenetic tree is reconstructed; and a display device to present the reconstructed predicted phylogenetic tree in determining closeness of relationship between species or individuals, based on the reconstructed phylogenetic tree topology.

28. The system as recited in claim 27, wherein the reconstructing further comprises using a four-point function from the samples of the characters of the one or more selected pairs.

29. The system as recited in claim 27, wherein the reconstructing further comprises:

reconstructing one or more levels of a predicted phylogenetic tree topology, yielding a reconstructed partial phylogenetic tree topology.

30. The system as recited in claim 27, wherein the estimating further comprises using a majority function.

31. A system to reconstruct a tree from a plurality of known leaf nodes of the tree:

a processor; and a memory to store the plurality of known leaf nodes of the phylogenetic tree, each known leaf node having a sequence of characters, the memory containing instructions that causes the processor to perform actions comprising:

reconstructing a predicted phylogenetic tree topology from samples of the sequence of characters of each of the plurality of known leaf nodes by:

identifying each of the samples including a number of characters;

calculating the number of characters being approximately equal to a factor of a natural logarithm of the number of the plurality of known nodes;

yielding a reconstructed phylogenetic tree topology having one or more nodes;

estimating a sequence of characters of each of the one or more nodes in the reconstructed phylogenetic tree topology in accordance with a stochastic mutation model from a majority function; and a display device to present the reconstructed phylogenetic tree topology to represent an evolution in determining how closely related species or individuals are, based on the reconstructed phylogenetic tree.

32. The system as recited in claim 31, wherein the stochastic mutation model further comprises a Cavender, Farris and Neyman model.

33. The system as recited in claim 31, wherein the reconstructing further comprises:

identifying one or more pairs of the plurality of known leaf nodes from the samples of characters of the plurality of known leaf nodes;

calculating a distance for each of the one or more identified pairs from the samples of characters of the one or more identified pairs;

selecting one or more of the identified pairs of the plurality of known leaf nodes that are within a predetermined threshold distance; and reconstructing one or more levels of a predicted phylogenetic tree topology from the samples of the sequence of characters of the one or more selected pairs of known leaf nodes.

34. The system as recited in claim 31, further comprising:

performing the reconstructing and the estimating iteratively until an entire free topology is reconstructed.

35. The system as recited in claim 31, wherein:

the reconstructing further comprises reconstructing a first portion of the reconstructed phylogenetic tree topology having one or more nodes;

the estimating further comprises estimating characters of each of the one or more nodes in the first portion of the reconstructed phylogenetic tree topology, and the memory further comprises instructions that causes the processor to perform actions comprising:

reconstructing one or more levels of a reconstructed phylogenetic tree topology from samples of the characters of the first portion of the reconstructed phylogenetic tree topology, wherein the partial phylogenetic tree topology comprises a second portion of the reconstructed phylogenetic tree topology having one or more nodes; and estimating characters of each of the one or more nodes in the second portion of the reconstructed phylogenetic tree topology.

* * * * *